United States Patent [19]

Machin

[11] 4,387,100
[45] Jun. 7, 1983

[54] SUBSTITUTED PHENOXY-AMINOPROPANOL DERIVATIVES

[75] Inventor: Peter J. Machin, London, England

[73] Assignee: Hoffmann-La Roche Inc., Nutley, N.J.

[21] Appl. No.: 237,612

[22] Filed: Feb. 24, 1981

[30] Foreign Application Priority Data

Feb. 25, 1980 [GB] United Kingdom ................. 8006261
Nov. 10, 1980 [GB] United Kingdom ................. 8035997

[51] Int. Cl.³ .................... A61K 31/41; A61K 31/415; C07D 233/61; C07D 249/08
[52] U.S. Cl. .................................. 424/269; 548/374; 548/375; 424/273 R; 548/377; 548/378; 424/273 B; 564/349; 424/273 P; 424/273 N; 542/469; 542/470; 548/255; 548/257; 548/259; 548/260; 548/261; 548/262; 548/263; 548/265; 548/269; 548/325; 548/326; 548/327; 548/329; 548/331; 548/333; 548/334; 548/335; 548/336; 548/337; 548/341; 548/343; 548/369; 548/371; 548/372; 548/373
[58] Field of Search ............... 548/378, 325, 326, 329, 548/333, 331, 334, 335, 337, 341, 343, 255, 257, 259, 260, 261, 262, 263, 265, 269, 369, 371, 372, 373, 375, 377; 424/273 P, 269, 273 R, 273 B, 273 N; 542/469, 470; 564/349

[56] References Cited

U.S. PATENT DOCUMENTS 3,432,545  3/1969  Howe et al. ......................... 564/349
3,723,476  3/1973  Nakanishi et al. ................... 564/349
4,263,325  4/1981  Carlsson et al. ..................... 564/349

Primary Examiner—Alton D. Rollins
Attorney, Agent, or Firm—Jon S. Saxe; Bernard S. Leon; William G. Isgro

[57] ABSTRACT

Phenoxy-aminopropanol derivatives of the formula

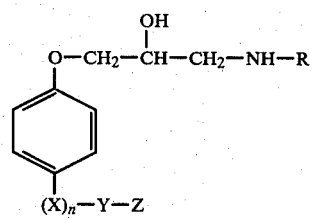

wherein R is lower alkyl, X is oxygen or sulfur, n is the integer zero or 1, Y is methylene, ethylene or propylene or, when n is zero, Y can also be a group of the formula

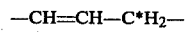 (a)

, wherein the double-bond is trans and the carbon atom marked with an asterisk is linked to Z, and Z is a 5-membered aromatic heterocyclic ring which contains one or more nitrogen atoms as the sole hetero atom (s), said heterocyclic ring is linked to Y via a nitrogen atom, and may be substituted by halogen, lower alkyl, lower alkoxy, aryl, cyano or carboxamido, or on adjacent carbon atoms by a group of the formula

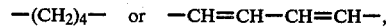

(b)         (c)

and pharmaceutically acceptable acid addition salts thereof are described. A process for the preparation of the compound of formula I and pharmaceutical preparations containing them are also described. The aforementioned compounds and salts possess β-adrenergic blocking activity and antihypertensive activity.

10 Claims, No Drawings

SUBSTITUTED PHENOXY-AMINOPROPANOL DERIVATIVES

BRIEF SUMMARY OF THE INVENTION

This invention relates to compounds of the formula

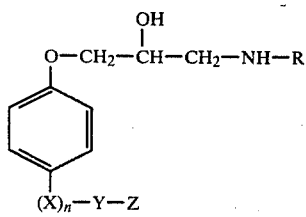

wherein R is lower alkyl, X is oxygen or sulfur, n is the integer zero or 1, Y is methylene, ethylene or propylene or, when n is zero, Y can also be a group of the formula

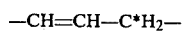

wherein the double-bond is trans and the carbon atom marked with an asterisk is linked to Z, and Z is a 5-membered aromatic heterocyclic ring which contains one or more nitrogen atoms as the sole hetero atom(s), said heterocyclic ring is linked to Y via a nitrogen atom and may be substituted by halogen, lower alkyl, lower alkoxy, aryl, cyano or carboxamido or on adjacent carbon atoms by a group of the formula

and pharmaceutically acceptable acid addition salts thereof, are described. A process for preparation of the compounds of formula I and pharmaceutical preparations containing them are also described. The phenoxy-aminopropanol compounds and salts possess β-adrenergic blocking activity and antihypertensive activity.

DETAILED DESCRIPTION OF THE INVENTION

The substituted phenoxy-aminopropanol derivatives of the invention are compounds of the formula

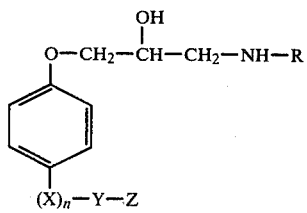

wherein R is lower alkyl, X is oxygen or sulfur, n is the integer zero or 1, Y is methylene, ethylene or propylene or, when n is zero, Y can also be a group of the formula

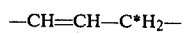

wherein the double-bond is trans and the carbon atom marked with an asterisk is linked to Z, and Z is a 5-membered aromatic heterocyclic ring which contains one or more nitrogen atoms as the sole hetero atom(s), said heterocyclic ring is linked to Y via a nitrogen atom and may be substituted by halogen, lower alkyl, lower alkoxy, aryl, cyano or carboxamido or, on adjacent carbon atoms, by a group of the formula

and their pharmaceutically acceptable acid addition salts.

As used herein, the term "lower alkyl" denotes straight-chain or branched-chain alkyl which preferably contains from 1 to 4 carbon atoms, for example, methyl, ethyl, propyl, isopropyl, butyl and tert.butyl. The term "lower alkoxy," as used herein, denotes straight-chain or branched-chain alkoxy which preferably contains from 1 to 4 carbon atoms, for example, methoxy, ethoxy, propoxy, and isopropoxy. As used herein, the term "halogen" denotes fluorine, chlorine bromine and iodine. The term "aryl" as used herein, denotes phenyl. As used herein aromatic heterocyclic ring denoted by Z include 1-imidazolyl, 1H-1,2,4-triazol-1-yl, 1H-1,2,3-triazol-yl, 2H-1,2,3-triazol-2-yl, 1-pyrazolyl, 4-halo-1-pyrazolyl (e.g. 4-chloro-1-pyrazolyl), 4-aryl-1-pyrazolyl (e.g. 4-phenyl-1-pyrazolyl), 1-benzimidazolyl, 2H-benzotriazol-2-yl, 4,5,6,7-tetrahydro-2H-benzotriazol-2-yl, 1H-indazol-1-yl and the like.

A preferred class of compounds of formula I comprises those in which R is an isopropyl or tert.butyl group, X is oxygen, n is 1 and Y is methylene. Also preferred are those compounds of formula I in which Z is 1-imidazolyl, 1H-1,2,4-triazol-1-yl, 2H-1,2,3-triazol-2-yl, 1-pyrazolyl or 4-halo-1-pyrazolyl group. From the above it follows that a more preferred class of compounds of formula I comprises those in which R is isopropyl, X is oxygen, n is 1, Y is methylene and Z is 2H-1,2,3-triazol-2-yl or 4-chloro-1-pyrazolyl group.

Examples of preferred compounds of formula I are:

1-Isopropylamino-3-[4-[2-(1-pyrazolyl)ethoxy]phenoxy]-2-propanol,

1-[4-[2-(1-imidazolyl)ethoxy]phenoxy]-3-isopropylamino-2-propanol,

1-[4-[2-(1-benzimidazolyl)ethoxy]phenoxy]-3-isopropylamino-2-propanol, 1-isopropylamino-3-[4-[2-(1H-1,2,4-triazol-1-yl)ethoxy]phenoxy]-2-propanol, 1-tert.butylamino-3-[4-[2-(1-pyrazolyl)ethoxy]phenoxy]-2-propanol, 1-isopropylamino-3-[4-[3-(1-pyrazolyl)propoxy]-phenoxy]-2-propanol, 1-isopropylamino-3-[4-[3-(1H-1,3,4-triazol-1-yl)propoxy]phenoxy]-2-propanol, 1-isopropylamino-3-[4-[2-(4-phenyl-1-pyrazolyl)ethoxy]phenoxy]-2-propanol, 1-isopropylamino-3-[4-[2-(4-chloro-1-pyrazolyl)ethoxy]phenoxy]-2-propanol, 1-[4-[2-(1-imidazolyl)ethyl]phenoxy]-3-isopropylamino-2-propanol, 1-isopropylamino-3-[4-[2-(1-pyrazolyl)ethyl]phenoxy]-2-propanol, 1-isopropylamino-3-[4-[2-(1H-1,2,4-triazol-1-yl)ethyl]phenoxy]-2-propanol, 1-isopropylamino-3-[4-[(1-pyrazolyl)methyl]phenoxy]-2-propanol, 1-[4-[2-(1-imidazolyl)methyl]phenoxy]-3-isopropylamino-2-propanol, 1-[4-[2-(2H-benzotriazol-2-yl)ethoxy]phenoxy]-3-isopropylamino-2-propanol,
1-[4-[2-(4,5,6,7-tetrahydro-2H-benzotriazol-2-yl)ethoxy]phenoxy]-2-propanol,
1-isopropylamino-3-[4-[3-(1-pyrazolyl)propyl]phenoxy]-2-propanol,
trans-1-isopropylamino-3-[4-[3-(1-pyrazolyl)-1-propenyl]phenoxy]-2-propanol,
1-isopropylamino-3-[4-[2-(1-pyyrazolyl)ethylthio]phenoxy]-2-propanol and
1-[4-[2-(1H-indazol-1-yl)ethoxy]phenoxy]-3-isopropylamino-2-propanol.

Further particularly preferred compounds of formula I are:

1-Isopropylamino-3-[4-[2-(2H-1,2,3-triazol-2-yl)ethoxy]phenoxy]-2-propanol,
1-isopropylamino-3-[4-[(1-pyrazolyl)methoxy]phenoxy]-2-propanol,
1-[4-[2-hydroxy-3-(isopropylamino)propoxy]phenoxymethyl]-4-pyrazolecarbonitrile,
1-isopropylamino-3-[4-[(1H-1,2,3-triazol-1-yl)methoxy]phenoxy]-2-propanol and
1-isopropylamino-3-[4-[(1-pyrazolyl)methylthio]phenoxy]-2-propanol.

Especially preferred compounds of formula I hereinbefore are:

1-[4-[(4-Chloro-1-pyrazolyl)methoxy]phenoxy]-3-isopropylamino-2-propanol and
1-isopropylamino-3-[4-[(2H)-1,2,3-triazol-2-yl)methoxy]phenoxy]-2-propanol.

According to the process of the invention, the substituted phenoxy-aminopropanol derivatives of formula I and their pharmaceutically acceptable acid addition salts are manufactured by (a) reacting an epoxide of the formula

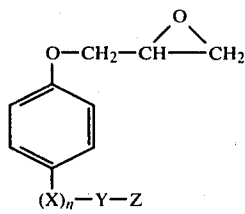

 II

Wherein X, Y, Z and n are as previously described, with an amine of the formula

R—NH$_2$   III wherein R is as previously described, or (b) for the preparation of a compound of formula I in which X is oxygen, n is 1 and Y is methylene, ethylene or propylene, reacting an alkali metal derivative of a phenol of the formula

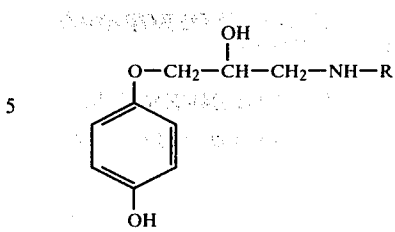

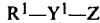 IV wherein R is as previously described, with a compound of the formula

R$^1$—Y$^1$—Z   V wherein R$^1$ is a leaving atom or group, Y$^1$ is methylene, ethylene or propylene and Z is as previously described, and/or (c) if desired, resolving a racemate of formula I into its optical isomers, and/or (d) if desired, converting a compound of formula I into a pharmaceutically acceptable acid addition salt.

The reaction of an epoxide of formula II with an amine of formula III, which is a known compound or can be prepared according to known procedures, in accordance with embodiment (a) of the process is carried out in a known manner. The reaction can be carried out in the presence or absence of an inert organic solvent. When an inert organic solvent is used, a lower alkanol, such as methanol, ethanol or the like can be suitably used. Alternatively, an excess of an amine of formula III can be used and can serve as the solvent. The reaction is advantageously carried out at a temperature in the range of from about 0° C. to about room temperature, preferably at room temperature, and under atmospheric pressure.

The leaving atom or group denoted by R$^1$ in a compound of formula V can be any conventional leaving atom or group; for example, a chlorine or bromine atom, a lower alkyl-sulfonyloxy group, for example, methanesulfonyloxy or an arylsulfonyloxy group, for example p-toluenesulfonyloxy. Preferably R$^1$ represents an arylsulfonyloxy group, especially p-toluenesulfonyloxy.

The reaction of an alkali metal derivative of a phenol of formula IV with a compound of formula V in accordance with embodiment (b) of the process is conveniently carried out in an inert organic solvent. Examples of inert organic solvents which can be used are dimethylformamide, dioxan, dimethoxyethane and tetrahydrofuran, with dimethyl-formamide being preferred. The alkali metal derivative of a phenol or formula IV is preferably formed in situ from a corresponding phenol and an alkali metal, an alkali metal hydride or an alkali metal amide, preferably an alkali metal hydride, for example sodium hydride. The reaction is advantageously carried out at an elevated temperature, preferably at about 60° C.

The compounds of formula I contain an asymmetric carbon atoms and can, therefore, occur in racemic or optically active form. The invention includes within its scope the racemates as well as the optically active forms. If desired, a racemate can be resolved into the optical isomers in accordance with embodiment (c) of the process using methods known per se; for example, by fractional crystallization of a salt formed with an optically active acid. The phenol starting material of formula IV can be used in optically active form to give a corresponding optically active form of the desired compound of formula I.

The compounds of formula I can be converted into pharmaceutically acceptable acid addition salts in accordance with embodiment (d) of the process by treatment with a pharmaceutically acceptable inorganic acid, for example hydrochloric acid, hydrobromic acid, sulphuric acid, phosphoric acid or the like, or with a pharmaceutically acceptable organic acid for example acetic acid, tartaric acid, citric acid, fumaric acid, maleic acid, malic acid, methanesulfonic acid, paratoluenesulfonic acid and the like.

The epoxides of formula II used as starting materials in embodiment (a) of the process are novel and also form part of the invention. They can be prepared by reacting an alkali metal derivative of a phenol of the formula

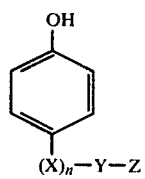

VI wherein X, Y, Z and n are as previously described, with epichlorohydrin or epibromohydrin.

The reaction of an alkali metal derivative of a phenol of formula VI with epichlorohydrin or epibromohydrin, preferably epichlorohydrin, can be carried out in a manner analogous to that described earlier in connection with the reaction of an alkali metal derivative of a phenol of formula IV with a compound of formula V.

The phenols of formula VI, many of which are novel and also form part of this invention, can be prepared in various ways depending on the significance of X, Y and n.

Thus, for example, phenols of formula VI in which X is oxygen, Y is ethylene or propylene and n is 1 can be prepared as illustrated in Reaction Scheme I hereinafter in which Z is as previously described, $Y^2$ is ethylene or propylene and Bz is a benzyl group.

Reaction Scheme I

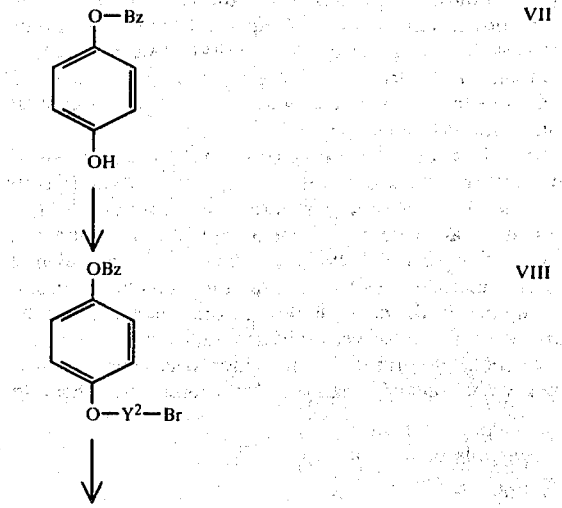

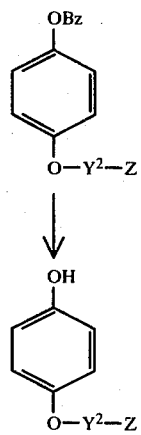

In connection with Reaction Scheme I, 4-benzyloxyphenol of formula VIII is reacted with a compound of the formula $Br-Y^2-Br$  X wherein $Y^2$ is as previously described, to give a compound of formula VIII. This reaction is carried out in a known manner; for example, in an aqueous-alkaline medium such as an aqueous alkali metal hydroxide, for example aqueous sodium hydroxide, at an elevated temperature, for example about 100° C.

A compound of formula VIII is subsequently converted into a compound of formula IX by reaction with a heterocyclic compound of the formula

H—Z  XI wherein Z is as previously described. This reaction is carried out in a conventional manner; for example, in the presence of an inert organic solvent such as dimethylformamide and the like, and in the presence of an appropriate alkali metal base such as an alkali metal hydride, for example sodium hydride. Conveniently, the reaction is carried out at an elevated temperature, for example about 60° C.

Finally, a compound of formula IX is converted into a desired phenol of formula VIa by debenzylation. The debenzylation can be carried out in a known manner, for example, using hydrogen in the presence of a catalyst, for example, palladium/carbon and the like, or using hydrogen bromide in glacial acetic acid.

Phenols of formula VI in which X represents an oxygen atom and n stands for 1 can be prepared by reacting an alkali metal derivative of 4-benzyloxyphenol of formula VII with a compound of formula V hereinbefore, preferably a chloride, and debenzylating the reaction product in a manner analogous to that described earlier in connection with the debenzylation of a compound of formula IX.

Reaction Scheme II illustrates the preparation of phenols of formula VI in which n is zero and Y is ethylene. In this Reaction Scheme, Z and Bz are as previously described and $R^2$ is lower alkyl or aryl.

Reaction Scheme II

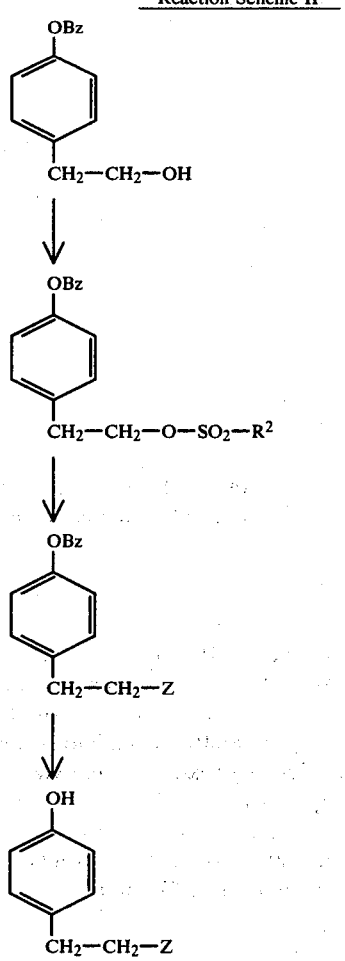

Reaction Scheme III

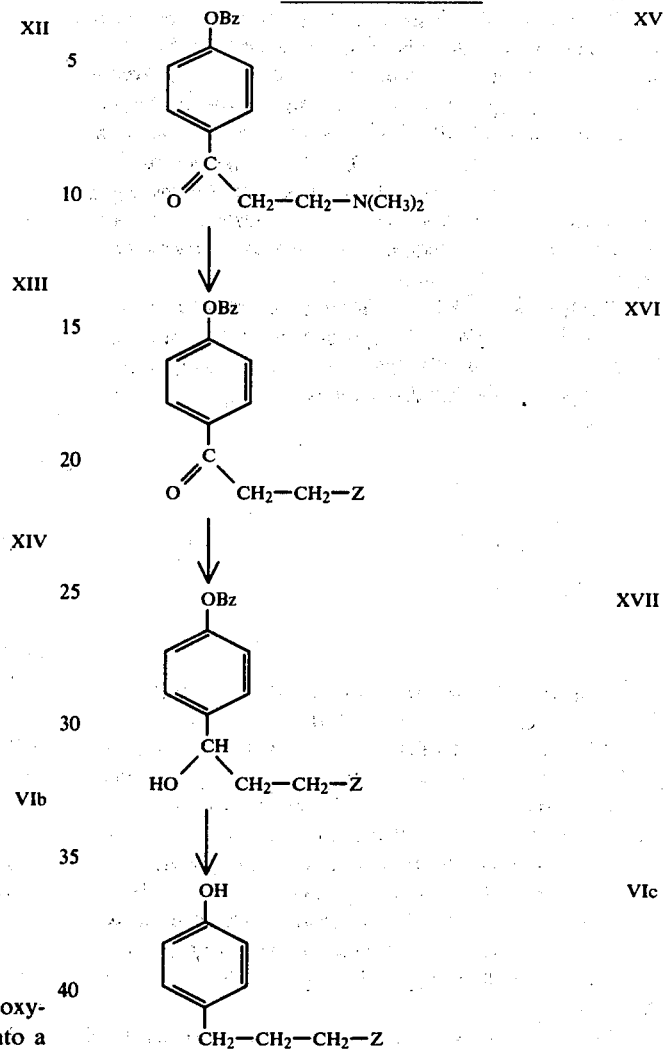

In connection with Reaction Scheme II, 4-benzyloxyphenethyl alcohol of formula XII is converted into a compound of formula XIII by reaction with a lower alkylsulfonyl or arylsulfonyl halide, preferably methanesulfonyl chloride. The reaction is conveniently carried out in the presence of an inert organic solvent, for example, an ether such as diethyl ether, and in the presence of an acid-binding agent, preferably a tertiary organic base such as pyridine and the like. Suitably, the reaction is carried out at a temperature below room temperature, particularly at about 0° C.

A compound of formula XIII is subsequently converted into a compound of formula XIV by reaction with a heterocyclic compound of formula XI in a manner analogous to that described earlier in connection with the reaction of a compound of formula VIII with such a heterocyclic compound.

Debenzylation of a compound of formula XIV in a manner analogous to that described earlier in connection with the debenzylation of a compound of formula IX yields a desired phenol of formula VIb.

Phenols of formula VI in which n is zero and Y is propylene can be prepared, for example, as illustrated in Reaction Scheme III in which Z and Bz are as previously described.

In the first step of Reaction Scheme III, 1-dimethylamino-3-(4-benzyloxyphenyl)propan-3-one of formula XV is reacted with a heterocyclic compound of formula XI to give a compound of formula XVI. This reaction is carried out in a conventional manner; for example, by heating the reactants together in an appropriate alkanol, for example n-butanol. The heating is suitably carried out at the reflux temperature of the reaction mixture.

A resulting compound of formula XVI is then converted into a compound of formula XVII by reduction in a known manner. For example, the reduction can be carried out using an alkali metal borohydride such as sodium borohydride in the presence of an inert organic solvent such as a lower alkanol, for example ethanol, at about room temperature.

Finally, a desired phenol of formula VIc is obtained from a compound of formula XVII by catalytic hydrogenation under acidic conditions. The catalytic hydrogenation can be carried out in a conventional manner in an inert organic solvent, for example a lower alkanol such as methanol, using, for example, palladium/carbon or the like as the catalyst. The acidic conditions can be provided, for example, by hydrochloric acid.

Phenols of formula VI in which n is zero and Y is methylene can be prepared, for example, by heating 4-hydroxybenzyl alcohol with a heterocyclic compound of formula XI in a known manner, for example at about 160° C.

Phenols of formula VI in which X represents a sulfur atom and n is 1 can be prepared, for example, by reacting 4-mercaptophenol with a compound of formula V.

The reaction of 4-mercaptophenol with a compound of formula V can be carried out in a conventional manner, for example, in the presence of inert organic solvent such as dimethylformamide and the like and in the presence of a suitable alkali metal base such as an alkali metal hydride, for example sodium hydride, or an alkali metal carbonate, for example potassium carbonate, at about room temperature.

Phenols of formula VI in which n is zero and Y is group of formula (a) can be prepared, for example, as illustrated in Reaction Scheme IV in which Z and Bz are as previously described and Et is ethyl.

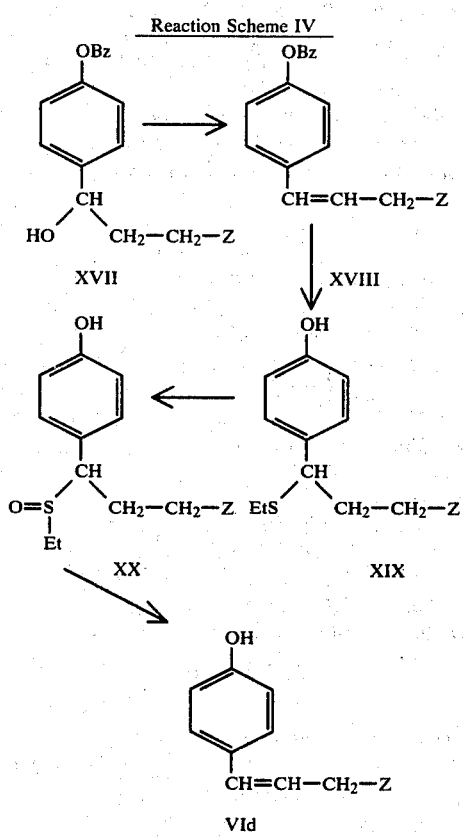

In connection with Reaction Scheme IV, a compound of formula XVII, prepared as described earlier in Reaction Scheme III, is firstly converted into a compound of formula XVIII by dehydration which can be carried out, for example, by heating with a lower alkylsulphonyl or arylsulphonyl chloride, preferably methanesulphonyl chloride in the presence of a tertiary organic base, preferably pyridine. The heating is advantageously carried out at about 100° C.

A compound of formula XVIII is subsequently converted into a compound of formula XIX by treatment with ethanethiol and boron trifluoride diethyl etherate. The treatment is suitably carried out at about room temperature.

The oxidation of a compound of formula XIX to give a compound of formula XX is conveniently carried out using an organic peracid in the presence of an inert organic solvent. Suitable organic peracids which can be used are peracetic acid, perbenzoic acid, halogenated perbenzoic acids, preferably m-chloroperbenzoic acid, monoperphthalic acid and the like. The inert organic solvent can be, for example, a halogenated hydrocarbon such as methylene chloride or the like.

Finally, a compound of formula XX is converted into a desired phenol of formula VId by heating in an inert organic solvent. The preferred inert organic solvents are aromatic hydrocarbons, especially toluene. The reaction is expediently carried out at the reflux temperature of the mixture.

The starting materials required in the methods described earlier for the preparation of phenols of formula VI are known compounds or analogues of known compounds which can be prepared in a customary manner.

The phenols of formula IV as well as the compounds of formula V which are used as starting materials in embodiment (b) of the process provided by the invention are known compounds or analogues of known compounds which can be prepared in a customary manner.

The substituted phenoxy-aminopropanol derivatives provided by the invention possess cardioselective $\beta$-adrenergic blocking activity. Accordingly, they can be used for the prophylaxis and treatment of diseases of the heart, such as, for example, angina pectoris and cardiac arrhythmias. They may also be used as antihypertensive agents.

The cardioselective $\beta$-blocking activity of the substituted phenoxy-aminopropanol derivatives of formula I at $\beta_1$- and $\beta_2$-adrenoceptors can be demonstrated using standard test procedures. In one such test procedure, this activity is measured in rats by determining the dosage in $\mu$g/kg i.v. of substance being tested which is required to produce a 50% reduction in isoprenaline-induced tachycardia, this dosage being expressed at the $ED_{50}(HR)$, and a 50% reduction in isoprenaline-induced depressor responses, this dosage being expressed as the $ED_{50}(BP)$. Where the $ED_{50}(BP)$ is significantly greater than the $ED_{50}(HR)$, the test substance is more selective in blocking $\beta_1$- than $\beta_2$-adrenoceptors, i.e. is cardioselective.

The results obtained in the foregoing test with representative substituted phenoxy-aminopropanol derivatives of formula I provided by the invention and atenolol, a well-known and widely used cardioselective $\beta$-adrenergic blocking agent, are given in the following Table.

TABLE

| Derivative | $ED_{50}$ (HR) ($\mu$g/kg i.v.) | $ED_{50}$ (BP) ($\mu$g/kg i.v.) |
|---|---|---|
| A | 50 | 6500 |
| B | 4 | 2430 |
| C | 11 | >2000 |
| D | 14 | >2000 |
| Atenolol | 91 | 2130 |

Derivative A: 1-Isopropylamino-3-[4-[2-(1-pyrazolyl)ethoxy]phenoxy]-2-propanol hydrogen maleate.
Derivative B: 1-[4-[(4-Chloro-1-pyrazolyl)methoxy]phenyl]-3-isopropylamino-2-propanol hydrogen oxalate.
Derivative C: 1-Isopropylamino-3-[4-[2-(2H—1,2,3-triazolo-2-yl)methoxy]phenoxy]-2-propanol hydrochloride.
Derivative D: 1-Isopropylamino-3-[4-[2-[2H—1,2,3-triazol-2-yl)ethoxy]phenoxy]-2-propanol hydrochloride.

The substituted phenoxy-aminopropanol derivatives of formula I and their pharmaceutically acceptable addition salts may be used as medicaments, in the form of pharmaceutical preparations which contain them in association with a compatible pharmaceutical carrier material. Such carrier material can be an inert organic or inorganic carrier material suitable for parenteral or enteral, for example, oral, administration. Examples of such carrier materials are water, gelatin, talc, starch, magnesium stearate, gum arabic, vegetable oils, polyalkylene-glycols, petroleum jelly and the like. The pharmaceutical preparations can be prepared in a conventional manner and finished dosage forms can be solid dosage forms, for example, tablets, dragees, suppositories, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like.

The substituted phenoxy-aminopropanol derivatives of formula I provided by the invention may be administered to warm blooded animals in an amount in the range of from approximately 1 mg/kg to 10 mg/kg, per day in a single dose or in divided doses. It is understood that this dosage range is given by way of example and that it can be varied upwards or downwards depending on factors such as the particular substituted phenoxyaminopropanol derivative being administered, the route of administration and the needs and requirements of the warm blooded animal as determined by the attending physician.

The following examples illustrate the invention. All parts are by weight, and all temperatures are in degrees centigrade, unless otherwise mentioned.

EXAMPLE 1

Preparation of
1-isopropylamino-3-[4-[2-(1-pyrazolyl)ethoxy]phenoxy]-2-propanol hydrogen maleate 3.16 g of 4-[2-(1-pyrazolyl)ethoxy]phenol were dissolved in 75 ml of dimethylformamide, and the solution was stirred for 5 minutes with 0.72 g of a 50% sodium hydride dispersion in mineral oil. 10 ml of epichlorohydrin were added, and the solution was stirred at 60° C. for 30 minutes. The solvent and excess epichlorohydrin were removed by evaporation under reduced pressure, and the residue was partitioned between ethyl acetate and water. The organic phase was separated, dried over sodium sulfate, filtered, and evaporated to give 4.1 g of crystalline epoxide which, without further purification, was dissolved in 100 ml of ethanol containing 15 ml of isopropylamine. The mixture was then left to stand at room temperature overnight. The solution was evaporated to dryness, and the crystalline product was dissolved in 100 ml of ethanol containing 1.74 g of maleic acid. The solution was evaporated, and the residue was recrystallized from isopropanol, whereby 5.0 g (76.5%) of 1-isopropylamino-3-[4-[2-(1-pyrazolyl)ethoxy]phenoxy]-2-propanol hydrogen maleate having a melting point of 103°–105° C. were obtained.

The 4-[2-(1-pyrazolyl)ethoxy]phenol used as the starting material can be prepared as follows:

(a) 125 ml of 1.6 N sodium hydroxide solution were added over a period of 1 hour to a vigorously stirred mixture of 40 g of 4-benzyloxyphenol and 71.1 g of ethylene dibromide at 100° C. and stirring was continued at 100° C. overnight. The cooled mixture was partitioned between 20% aqueous sodium hydroxide and diethyl ether. The organic phase was separated, washed with water, dried over sodium sulfate, filtered, and evaporated to dryness. After recrystallization of the residue, 36 g (59%) of 1-benzyloxy-4-(2-bromoethoxy)benzene having a melting point of 77°–80° C. were obtained.

(b) A solution of 1.36 g of pyrazole in 50 ml of dimethylformamide was treated with 0.96 g of a 50% sodium hydride dispersion in mineral oil, and the mixture was stirred for 5 minutes. 6.14 g of 1-benzyloxy-4-(2-bromoethoxy)benzene were added, and the mixture was heated at 60° C. for 0.5 hour while stirring. The solvent was removed by evaporation under reduced pressure, and the residue was partitioned between ethyl acetate and water. The organic phase was separated, washed with water, dried over sodium sulfate, and evaporated to give 5.7 g of a crystalline residue. This residue was dissolved in 250 ml of ethanol and hydrogenated overnight at atmospheric pressure and room temperature in the presence of 0.2 g of 10% palladium/carbon. The catalyst was removed by filtration, the solvent was evaporated, and the residue was recrystallized from toluene, whereby 3.16 g (77.5%) of 4-[2-(1-pyrazolyl)ethoxy]phenol having a melting point of 74°–77° C. were obtained.

EXAMPLE 2

Preparation of
1-[4-[2-(1-imidazolyl)ethoxy]phenol]-3-isopropylamino-2-propanol bis(hydrogen oxalate)

In a manner analogous to that described in the first paragraph of Example 1, from 4-[2-(1-imidazolyl)ethoxy]phenol, 1-[4-[2-(1-imidazolyl)ethoxy]phenoxy]-3-isopropylamino-2-propanol bis(hydrogen oxalate) having a melting point of 147°–148° C. (decomposition) (from methanol) was obtained.

The starting material can be prepared as follows:
In a manner analogous to that described in Example 1(b), from 1-benzyloxy-4-(2-bromoethoxy)benzene and imidazole, 4-[2-(1-imidazolyl)ethoxy]phenol having a melting point of 141°–144° C. was obtained.

EXAMPLE 3

Preparation of
1-[4-[2-(1-benzimidazolyl)ethoxy]phenoxy]-3-isopropylamino-2-propanol bis(hydrogen oxalate)

In a manner analogous to that described in the first paragraph of Example 1, from 4-[2-(1-benzimidazolyl)ethoxy]phenol, 1-[4-[2-(1-benzimidazolyl)ethoxy]phenoxy]-3-isopropylamino-2-propanol bis(hydrogen oxalate) having a melting point of 170°–173° C. (from ethanol) was obtained.

The starting material can be prepared as follows:
In a manner analogous to that described in Example 1(b), from 1-benzyloxy-4-(2-bromoethoxy)benzene and benzimidazole, 4-[2-(1-benzimidazolyl)ethoxy]phenol was obtained.

EXAMPLE 4

Preparation of
1-isopropylamino-3-[4-[2-(1H-1,2,4-triazol-1-yl)ethoxy]phenoxy]-2-propanol dihydrochloride In a manner analogous to that described in the first paragraph of Example 1, from 4-[2-(1H-1,2,4-triazol-1-yl)ethoxy]phenol, 1-isopropylamino-3-[4-[2-(1H-1,2,4- triazol-1-yl)ethoxy]phenoxy]-2-propanol dihydrochloride having a melting point of 153°-158° C. (from isopropanol/ethanol) was obtained.

The starting material can be prepared as follows:

In a manner analogous to that described in Example 1(b), from 1-benzyloxy-4-(2-bromoethoxy)benzene and 1H-1,2,4-triazole, 4-[2-(1H-1,2,4-triazol-1-yl)ethoxy]phenol was obtained.

EXAMPLE 5

Preparation of 1-tert.butylamino-3-[4-[2-(1-pyrazolyl)ethoxy]phenoxy]-2-propanol hydrogen maleate In a manner analogous to that described in the first paragraph of Example 1, but using tert.-butylamine in place of isopropylamine, 1-tert.butylamino-3-[4-[2-(1-pyrazolyl)ethoxy]-2-propanol hydrogen maleate having a melting point of 145°-148° C. (from ethanol) was obtained.

EXAMPLE 6

Preparation of 1-isopropylamino-3-[4-[3-(1-pyrazolyl)propoxy]phenoxy]-2-propanol hydrogen maleate In a manner analogous to that described in the first paragraph of Example 1, from 4-[3-(1-pyrazolyl)propoxy]phenol, 1-isopropylamino-3-[4-[3-(1-pyrazolyl)propoxy]phenoxy]-2-propanol hydrogen maleate having a melting point of 89°-91° C. (from isopropanol) was obtained.

The starting material can be prepared as follows:

(a) In a manner analogous to that described in Example 1(a), from 4-benzyloxyphenol and 1,3-dibromopropane, 1-benzyloxy-4-(3-bromopropoxy)benzene having a melting point of 49°-53° C. (from methanol) was obtained.

(b) In a manner analogous to that described in Example 1(b), from 1-benzyloxy-4-(3-bromopropoxy)benzene and pyrazole, 4-[3-(1-pyrazolyl)propoxy]phenol having a melting point of 108°-110° C. was obtained.

EXAMPLE 7

Preparation of 1-isopropylamino-3-[4-[3-(1H-1,3,4-triazol-1-yl)propoxy]phenoxy]-2-propanol dihydrochloride In a manner analogous to that described in the first paragraph of Example 1, from 4-[3-(1H-1,2,4-triazol-1-yl)propoxy]phenol, 1-isopropylamino-3-[4-[3-(1H-1,3,4-triazol-1-yl)propoxy]phenoxy]-2-propanol dihydrochloride having a melting point of 158°-160° C. (from ethanol) was obtained.

The starting material can be prepared as follows:

In a manner analogous to that described in Example 1(b), from 1-benzyloxy-4-(3-bromopropoxy)benzene [prepared as described in Example 6(a)] and 1H-1,2,4-triazole, 4-[3-(1H-1,2,4-triazol-1-yl)propoxy]phenol having a melting point of 141°-144° C. was obtained.

EXAMPLE 8

Preparation of 1-isopropylamino-3-[4-[2-(4-phenyl-1-pyrazolyl)ethoxy]phenoxy]-2-propanol hydrogen maleate In a manner analogous to that described in the first paragraph of Example 1, from 4-[2-(4-phenyl-1-pyrazolyl)ethoxy]phenol, 1-isopropylamino-3-[4-[2-(4-phenyl-1-pyrazolyl)ethoxy]phenoxy]-2-propanol hydrogen maleate having a melting point of 141°-143° C. (from isopropanol) was obtained.

The starting material can be prepared as follows:

5.7 g of 1-benzyloxy-4-[2-(4-phenyl-1-pyrazolyl)ethoxy]benzene [prepared from 1-benzyloxy-4-(2-bromoethoxy)benzene and 4-phenylpyrazole in a manner analogous to that described in Example 1(b)] were stirred in 20 ml of 48% of hydrogen bromide in glacial acetic acid at 25° C. for 0.5 hour. The solution was evaporated to dryness, and the residue was partitioned between 2 N aqueous sodium hydroxide and diethyl ether. The aqueous phase was acidified to pH 6 with concentrated hydrochloric acid and extracted with ethyl acetate. The ethyl acetate extract was washed, dried over sodium sulfate, and filtered. The filtrate was evaporated. The residue was crystallized from toluene, whereby 3.24 g (75%) of 4-[2-(4-phenyl-1-pyrazolyl)ethoxy]phenol having a melting point of 146°-150° C. were obtained.

EXAMPLE 9

Preparation of 1-isopropylamino-3-[4-[2-(4-chloro-1-pyrazolyl)ethoxy]phenoxy]-2-propanol p-toluenesulfonate In a manner analogous to that described in the first paragraph of Example 1, from 4-[2-(4-chloro-1-pyrazolyl)ethoxy]phenol, 1-isopropylamino-3-[4-[2-(4-chloro-1-pyrazolyl)ethoxy]phenoxy]-2-propanol p-toluenesulfonate having a melting point of 120° C. (from ethanol) was obtained.

The starting material can be prepared as follows:

In a manner analogous to that described in the second paragraph of Example 8, from 1-benzyloxy-4-[2-(4-chloro-1-pyrazolyl)ethoxy]benzene [prepared from 1-benzyloxy-4-(2-bromoethoxy)benzene and 4-chloropyrazole in a manner analogous to that described in Example 1(b)], 4-[2-(4-chloro-1-pyrazolyl)ethoxy]phenol having a melting point of 105° C. (from carbon tetrachloride) was obtained.

EXAMPLE 10

Preparation of 1-[4-[2-(1-imidazolyl)ethyl]phenoxy]-3-isopropylamino-2-propanol bis(hydrogen maleate)

In a manner analogous to that described in the first paragraph of Example 1, from 2.82 g of 4-[2-(1-imidazolyl)ethyl]phenol, 5.57 g (69%) of 1-[4-[2-(1-imidazolyl)ethyl]phenoxy]-3-isopropylamino-2-propanol bis(hydrogen maleate) having a melting point of 104°-106° C. (from isopropanol) were obtained.

The starting material can be prepared as follows:

(a) A solution of 3.51 g of methanesulfonyl chloride in 5 ml of diethyl ether was added dropwise over a period of 0.5 hour to a stirred solution of 7.0 g of 4-benzyloxyphenethyl alcohol in 20 ml of pyridine at 0° C. Stirring was continued for 2 hours while the mixture was allowed to warm to room temperature: The mixture was then partitioned between 150 ml of 2 N hydrochloric acid and dichloromethane. The organic phase was separated, washed with water, dried over sodium sulfate, filtered, and evaporated. Trituration of the residue with n-hexane brought about crystallization. The crystals were removed by filtration and dried, whereby 8.9 g (95%) of 1-benzyloxy-4-(2-methanesulfonyloxyethyl)benzene having a melting point of 60°-64° C. were obtained.

(b) 1.93 g of imidazole of 100 ml of dimethylformamide were treated with 1.36 g of a 50% sodium hydride dispersion in mineral oil, and the mixture was stirred for 5 minutes. 8.65 g of 1-benzyloxy-4-(2-methanesulfonyloxyethyl)benzene were added, and the mixture was heated at 60° C. for 0.5 hour while stirring. The solvent was removed by evaporation under reduced pressure, the residue was triturated with water, removed by filtration, washed with water, and dried. The resulting solid (7.5 g) was dissolved in 200 ml of ethanol, and the solution was hydrogenated overnight at atmospheric pressure and room temperature in the presence of 0.2 g of 10% palladium/carbon. The catalyst was removed by filtration, the solvent was evaporated, and the residue was recrystallized from ethanol, whereby 3.36 g (67%) of 4-[2-(1-imidazolyl)ethyl]phenol having a melting point of 158°–161° C. were obtained.

EXAMPLE 11

Preparation of
1-isopropylamino-3-[4-[2-(1-pyrazolyl)ethyl]phenoxy]-2-propanol p-toluenesulfonate In a manner analogous to that described in the first paragraph of Example 1, from 4-[2-(1-pyrazolyl)ethyl]phenol, 1-isopropylamino-3-[4-[2-(1-pyrazolyl)ethyl]phenoxy]-2-propanol p-toluenesulfonate having a melting point of 134°–135° C. (from isopropanol) was obtained.

The starting material can be prepared as follows:

In a manner analogous to that described in Example 10(b), from pyrazole and 1-benzyloxy-4-(2-methanesulfonyloxyethyl)benzene, 4-[2-(1-pyrazolyl)ethyl]phenol having a melting point of 94°–95° C. was obtained.

EXAMPLE 12

Preparation of
1-isopropylamino-3-[4-[2-(1H-1,2,4-triazol-1-yl)ethyl]phenoxy]-2-propanol dihydrochloride In a manner analogous to that described in the first paragraph of Example 1, from 4-[2-(1H-1,2,4-triazol-1-yl)ethyl]phenol, 1-isopropylamino-3-[4-[2-(1H-1,2,4-triazol-1-yl)ethyl]phenoxy]-2-propanol dihydrochloride having a melting point of 173°–175° C. (from ethanol) was obtained.

The starting material can be prepared as follows:

In a manner analogous to that described in Example 10(b), from 1H-1,2,4-triazole and 1-benzyloxy-4-(2-methane-sulfonyloxyethyl)benzene, 4-[2-(1H-1,2,4-triazol-1-yl)ethyl]phenol was obtained.

EXAMPLE 13

Preparation of
1-isopropylamino-3-[4-[(1-pyrazolyl)methyl]phenoxy]-2-propanol hydrogen maleate In a manner analogous to that described in the first paragraph of Example 1, from 3.3 g of 4-[(1-pyrazolyl)methyl]phenol, 4.0 g (54%) of 1-isopropylamino-3-[4-[(1-pyrazolyl)methyl]phenoxy]-2-propanol hydrogen maleate having a melting point of 103°–105° C. (from isopropanol) were obtained.

The starting material can be prepared as follows:

4.96 g of 4-hydroxybenzyl alcohol and 2.72 g of pyrazole were heated together at 160° C. for 30 minutes. The resulting solid was cooled and dissolved in 150 ml of boiling toluene. The solution was decanted from a small quantity of black tar and then evaporated to dryness. After recrystallization of the residue from ethyl acetate, 3.3 g (47%) of 4-[(1-pyrazolyl)methyl]phenol having a melting point of 113°–115° C. were obtained.

EXAMPLE 14

Preparation of
1-[4-[(1-imidazolyl)methyl]phenoxy]-3-isopropylamino-2-propanol bis(hydrogen oxalate)

In a manner analogous to that described in the first paragraph of Example 1, from 4-[(1-imidazolyl)methyl]phenol, 1-[4-[(1-imidazolyl)methyl]phenoxy]-3-isopropylamino-2-propanol bis(hydrogen oxalate) having a melting point of 105°–107° C. (from methanol) was obtained.

The starting material can be prepared as follows:

In a manner analogous to that described in the second paragraph of Example 13, from 4-hydroxybenzyl alcohol and imidazole, 4-[(1-imidazolyl)methyl]phenol was obtained.

EXAMPLE 15

Preparation of
1-[4-[2-(2H-benzotriazol-2-yl)ethoxy]phenoxy]-3-isopropylamino-2-propanol hydrochloride In a manner analogous to that described in the first paragraph of Example 1, from 1.26 g of 4-[2-(2H-benzotriazol-2-yl)ethoxy]phenol, 1.23 g (62%) of 1-[4-[2-(2H-benzotriazol-2-yl)ethoxy]phenoxy]-3-isopropylamino-2-propanol hydrochloride having a melting point of 175°–176° C. (from methanol) were obtained.

The starting material can be prepared as follows:

(a) A solution of 5.95 g of benzotriazole in 100 ml of dimethylformamide was treated with 2.40 g of a 50% sodium hydride dispersion in mineral oil, and the mixture was stirred for 5 minutes. 15.35 g of 1-benzyloxy-4-(2-bromoethoxy)-benzene [prepared as described in Example 1(a)] were added, and the mixture was heated at 60° C. for 20 minutes while stirring. The solvent was removed by evaporation under reduced pressure, and the residue was partitioned between water and ethyl acetate. The organic phase was separated, washed with water, dried over sodium sulfate, and evaporated to give 17.5 g of a crystalline solid. This solid was chromatographed on a column of silica gel using 10% ethyl acetate/hexane for the elution. The eluate was evaporated, and after recrystallization from ethanol, 6.18 g of 1-benzyloxy-4-[2-(2H-benzotriazol-2-yl)ethoxy]benzene having a melting point of 105°–107° C. were obtained.

(b) 3.1 g of 1-benzyloxy-4-[2-(2H-benzotriazol-2-yl)ethoxy]benzene were debenzylated with 48% hydrogen bromide/acetic acid in a manner analogous to that described in the second paragraph of Example 8, wherein 1.26 g (55%) of 4-[2-(2H-benzotriazol-2-yl)ethoxy]phenol having a melting point of 98° C. (from isopropanol) were obtained.

EXAMPLE 16

Preparation of
1-[4-[2-(4,5,6,7-tetrahydro-2H-benzotriazol-2-yl)ethoxy]phenoxy]-3-isopropylamino-2-propanol hydrochloride In a manner analogous to that described in the first paragraph of Example 1, from 2.8 g of 4-[2-(4,5,6,7-tetrahydro-2H-benzotriazol-2-yl)ethoxy]phenol, 3.15 g of 1-[4-[2-(4,5,6,7-tetrahydro-2H-benzotriazol-2-yl)ethoxy]phenoxy]-3-isopropylamino-2-propanol hydrochloride having a melting point of 157°–158° C. (from acetonitrile) were obtained.

The starting material can be prepared as follows:

5.5 g of 1-benzyloxy-4-[2-(2H-benzotriazol-2-yl)ethoxy]benzene[prepared as described in Example 15(a)] were hydrogenated in a manner analogous to that described in Example 1(b) until no more hydrogen was taken up, whereby 2.8 g (69%) of 4-[2-(4,5,6,7-tetrahydro-2H-benzotriazol-2-yl)ethoxy]phenol having a melting point of 93° C. (from toluene) were obtained.

EXAMPLE 17

Preparation of 1-isopropylamino-3-[4-[3-(1-pyrazolyl)propyl]phenoxy]-2-propanol hydrogen maleate In a manner analogous to that described in the first paragraph of Example 1, from 8.5 g of 4-[3-(1-pyrazolyl)propyl]phenol, 10.90 g (60%) of 1-isopropylamino-3-[4-[3-(1-pyrazolyl)propyl]phenoxy]-2-propanol hydrogen maleate having a melting point of 126°–130° C. (from isopropanol) were obtained.

The starting material can be prepared as follows:

(a) 20 g of 1-dimethylamino-3-(4-benzyloxyphenyl)-propan-3-one and 6.8 g of pyrazole in 250 ml of n-butanol were heated under reflux for 15 hours, and the solution was then evaporated to dryness. The residue was partitioned between ethyl acetate and water. The organic phase was separated, dried over sodium sulfate, filtered, and evaporated. After recrystallization from ethyl acetate, 15.1 g (70%) of 1-(1-pyrazolyl)-3-(4-benzyloxyphenyl)-propan-3-one having a melting point of 111°–114° C. were obtained.

(b) The foregoing ketone was dissolved in 500 ml of ethanol, and the solution was stirred at room temperature for 16 hours with 2.0 g of sodium borohydride. The solvent was removed by evaporation, and the residue was partitioned between dichloromethane and water. The organic phase was dried over sodium sulfate, filtered, and evaporated, whereby 14.9 g (98%) of 1-benzyloxy-4-[1-hydroxy-3-(1-pyrazolyl)propyl]benzene having a melting point of 80°–85° C. were obtained.

(c) The foregoing alcohol was dissolved in 600 ml of ethanol containing 8 ml of concentrated hydrochloric acid, and the solution was hydrogenated at atmospheric pressure and room temperature in the presence of 0.4 g of 10% palladium/carbon. The catalyst was removed by filtration, the filtrate was evaporated, and the residue was partitioned between ethyl acetate and saturated sodium bicarbonate solution. The organic phase was separated, dried over sodium sulfate, filtered, and evaporated, whereby 8.5 g (87%) of 4-[3-(1-pyrazolyl)propyl]phenol in the form of a colorless oil which was used without further purification were obtained.

EXAMPLE 18

Preparation of 1-isopropylamino-3-[4-[2-(1-pyrazolyl)ethoxy]phenoxy]-2-propanol 113 mg of 1-isopropylamino-3-(4-hydroxyphenyl)-2-propanol in 1 ml of dimethylformamide were treated with 24 mg of a 50% sodium hydride dispersion in mineral oil, and the mixture was stirred for 5 minutes. 133 mg of 1-[2-(p-toluenesulfonyloxy)ethyl]pyrazole were added, and the mixture was heated at 60° C. for 20 minutes while stirring. The mixture was evaporated to dryness, and the residue was partitioned between 2 N sodium hydroxide solution and dichloromethane. The organic phase was separated, washed well with water, dried over sodium sulfate, filtered and evaporated, whereby crystalline 1-isopropylamino-3-[4-[2-(1pyrazolyl)ethoxy]phenoxy]-2-propanol which was converted into 154 mg (71%) of the maleate salt was obtained. This salt was identical with the product obtained according to the first paragraph of Example 1.

The 1-[2-(p-toluenesulfonyloxy)ethyl]pyrazole used as the starting material can be prepared as follows:

(a) 34 g of pyrazole and 50 g of ethylene carbonate were heated together at 160° C. for 1 hour. 52 g (93%) of 1-(2-hydroxyethyl)pyrazole, distilled directly from the mixture under a high vacuum having a boiling point of 80°–85° C./0.5 mmHg were obtained.

(b) 50 g of 1-(2-hydroxyethyl)pyrazole in 500 ml of pyridine were treated portionwise over a period of 20 minutes with 85.05 g of p-toluenesullfonly chloride. The mixture was stirred at 25° C. for 2 hours, the solvent was removed by evaporation, and the residue was partitioned between concentrated hydrochloric acid and diethyl ether. The aqueous phase was carefully made basic with saturated sodium bicarbonate solution and then extracted with ethyl acetate. The ethyl acetate extract was washed with 1 N hydrochloric acid and water, then separated, dried over sodium sulfate, filtered, and evaporated to give a low-melting solid residue. This residue was triturated with diethyl ether at −30° C., and the crystals were removed by filtration, whereby 46 g (39%) of 1-[2-(p-toluenesulfonyloxy)ethyl]-pyrazole having a melting point of 37°–39° C. were obtained.

EXAMPLE 19

Preparation of trans-1-isopropylamino-3-[4-[3-(1-pyrazolyl)-1-propenyl]phenoxy]-2-propanol hydrogen maleate In a manner analogous to that described in the first paragraph of Example 1, from 0.55 g of 4-[3-(1-pyrazolyl)prop-1-enyl]phenol, 0.76 g (64%) of trans-1-isopropylamino-3-[4-[3-(1-pyrazolyl)-1-propenyl]-phenoxy]-2-propanol hydrogen maleate having a melting point of 121°–125° C. (from isopropanol) was obtained.

The starting material can be prepared as follows:

(a) 8.8 g of 1-benzyloxy-4-[1-hydroxy-3-(1-pyrazolyl)propyl]benzene and 3.27 g of methanesulfonyl chloride were heated under reflux in pyridine for 15 hours, whereupon a further equivalent (3.27 g) of methanesulfonyl chloride was added, and the heating under reflux was continued for a further 15 hours. The pyridine was removed by evaporation, and the residue was partitioned between ethyl acetate and water. The organic phase was separated, dried over sodium sulfate, and filtered. The filtrate was evaporated, and the residue was recrystallized from methylcyclohexane, whereby 4.8 g (58%) of 1-benzyloxy-4-[3-(1-pyrazolyl)-prop-1-enyl]benzene having a melting point of 91°–93° C. were obtained.

(b) 4.51 g of 1-benzyloxy-4-[3-(1-pyrazolyl)prop-1-enyl]benzene were dissolved in a mixture of 25 ml of ethanethiol and 25 ml of boron trifluoride diethyl etherate, and the resulting mixture was stirred at 25° C. for 0.75 hours. The excess thiol was removed by evaporation, and the residue was partitioned between ethyl acetate and water. The organic phase was separated, dried over sodium sulfate, and filtered. The filtrate was evaporated, and the residue was chromatographed on silica gel using chloroform for the elution. The eluate was evaporated, whereby 3.5 g (86%) of 4-[1-ethylthio-3-(1-pyrazolyl)propyl]phenol in the form of an oil was obtained.

(c) 3.5 g of 4-[1-ethylthio-3-(1-pyrazolyl)propyl]phenol were dissolved in 100 ml of dichloromethane, and the solution was stirred for 0.25 hour with 2.81 g of m-chloroperbenzoic acid. The mixture was washed with saturated sodium bicarbonate solution, and the dichloromethane layer was separated, dried over sodium sulfate, and filtered. The filtrate was evaporated to give 3.5 g of the corresponding sulfoxide which was dissolved in 100 ml of toluene. This solution was heated under reflux for 24 hours and then evaporated to dryness. The residue was chromatographed on silica gel using chloroform/hexane (9:1) for the elution. After evaporation of the eluate, 0.55 g (22%) of 4-[3-(1-pyrazolyl)prop-1-enyl]phenol in the form of a yellow crystalline solid having a melting point of 146°–152° C. was obtained.

EXAMPLE 20

Preparation of
1-isopropylamino-3-[4-[2-(1-pyrazolyl)ethylthio]phenoxy]-2-propanol hydrogen maleate In a manner analogous to that described in Example 1, from 2.6 g of 4-[2-(1-pyrazolyl)ethylthio]phenol, 2.45 g (46%) of 1-isopropylamino-3-[4-[2-(1-pyrazolyl)ethylthio]phenoxy]-2-propanol hydrogen maleate having a melting point of 84°–86° C. were obtained.

The starting material can be prepared as follows:

3.15 g of 4-mercaptophenol in 75 ml of dimethylformamide were treated with 1.2 g of a 50% sodium hydride dispersion in mineral oil, and the mixture was stirred for 5 minutes. 6.65 g of 1-(2-p-toluenesulfonyloxyethyl)pyrazole in 20 ml of dimethylformamide were added, and the mixture was stirred at room temperature for 3 hours. The solvent was removed by evaporation, and the residue was partitioned between ethyl acetate and water. The organic phase was separated, dried over sodium sulfate, and filtered. The filtrate was evaporated, and the resulting solid was recrystallized from toluene, whereby 2.6 g (47%) of 4-[2-(1-pyrazolyl)ethylthio]phenol having a melting point of 87°–91° C. were obtained.

EXAMPLE 21

Preparation of
1-[4-[2-(1H-indazol-1-yl)ethoxy]phenoxy]-3-isopropylamino-2-propanol hydrochloride In a manner analogous to that described in the first paragraph of Example 1, from 1.90 g of 4-[2-(1H-indazol-1-yl)ethoxy]phenol, 1.50 g (49%) of 1-[4-[2-(1H-indazol-1-yl)ethoxy]phenoxy]-3-isopropylamino-2-propanol hydrochloride having a melting point of 121°–123° C. (from ethyl acetate) were obtained.

The starting material can be prepared as follows:

(a) 2.95 g of indazole were reacted with 7.68 g of 1-benzyloxy-4-(2-bromoethoxy)benzene [prepared as described in Example 1(a)] in a manner analogous to that described in Example 15(a), whereby 4.5 g (52%) of 1-benzyloxy-4-[2-(1H-indazol-1-yl)ethoxy]benzene having a melting point of 81°–83° C. (from hexane) were obtained.

(b) The benzyloxy compound obtained according to the preceding paragraph was debenzylated with 48% hydrogen bromide in glacial acetic acid in a manner analogous to that described in the second paragraph of Example 8, whereby 1.9 g (58%) of 4-[2-(1H-indazol-1-yl)ethoxy]phenol having a melting point of 124°–125° C. (from toluene) were obtained.

EXAMPLE 22

Preparation of
1-isopropylamino-3-[4-[2-(2H-1,2,3-triazol-2-yl)ethoxy]phenoxy]-2-propanol hydrochloride In a manner analogous to that described in the first paragraph of Example 1, from 5.1 g of 4-[2-(2H-1,2,3-triazol-2-yl)ethoxy]phenol, 4.50 g (51%) of 1-isopropylamino-3-[4-[2-(2H-1,2,3-triazol-2-yl)ethoxy]phenoxy]-2-propanol hydrochloride having a melting point of 119°–122° C. (from ethyl acetate) were obtained.

The starting material can be prepared as follows:

(a) 5.0 g of 1,2,3-triazole were reacted with 22.25 g of 1-benzyloxy-4-(2-bromoethoxy)benzene [prepared as described in Example 1(a)] in a manner analogous to that described in Example 15(a) to give 21.6 g of a solid consisting of a mixture of isomers. This solid was extracted with boiling petroleum ether (60°–80° C.), the extract was filtered, and the filtrate was cooled to bring about crystallization, whereby 9.54 g (45%) of 1-benzyloxy-4-[2-(2H-1,2,3-triazol-2-yl)ethoxy]benzene having a melting point of 97°–100° C. were obtained.

(b) The benzyloxy compound obtained according to the preceding paragraph was debenzylated by catalytic hydrogenation in a manner analogous to that described in Example 1(b), whereby 5.3 g (81%) of 4-[2-(2H-1,2,3-triazol-2-yl)ethoxy]phenol having a melting point of 63°–66° C. (from diethyl ether) were obtained.

EXAMPLE 23

Preparation of
1-isopropylamino-3-[4-[(1-pyrazolyl)methoxy]phenoxy]-2-propanol hydrogen maleate 675 mg of 1-isopropylamino-3-(4-hydroxyphenoxy)-2-propanol in 6 ml of dimethylformamide were treated with 288 mg of a 50% sodium hydride dispersion in mineral oil, and the mixture was stirred for 5 minutes. 459 mg of 1-chloromethylpyrazole hydrochloride were added, and the mixture was heated at 60° C. for 0.5 hour while stirring. The mixture was evaporated to dryness, and the residue was partitioned between 2 N sodium hydroxide solution and dichloromethane. The organic phase was separated, washed well with water, dried over sodium sulfate, filtered, and evaporated. The residue was treated with maleic acid in a manner analogous to that described in the first paragraph of Example 1, whereby 700 mg (56%) of 1-isopropylamino-3-[4-[(1-pyrazolyl)methoxy]phenoxy]-2-propanol hydrogen maleate having a melting point of 84°–87° C. (from isopropanol) were obtained.

EXAMPLE 24

Preparation of
1-[4-[(4-chloro-1-pyrazolyl)methoxy]phenoxy]-3-isopropylamino-2-propanol hydrogen fumarate In a manner analogous to that described in Example 18, from 3.02 g of 1-choromethyl-4-chloropyrazole, 5.6 g (61%) of 1-[4-[(4-chloro-1-pyrazolyl)methoxy]phenoxy]-3-isopropylamino-2-propanol hydrogen fumarate having a melting point of 82°–85° C. (from ethanol) were obtained. The corresponding hydrogen oxalate has a melting point of 71°–75° C. (decomposition) (from acetonitrile).

The 1-chloromethyl-4-chloropyrazole used as the starting material can be prepared as follows:

(a) 7.0 g of 4-chloropyrazole and 10.5 ml of 40% formalin solution in 70 ml of tetrahydrofuran were left to stand at 25° C. for 2 hours. The solution was evaporated to dryness, and the residue was partitioned between water and dichloromethane. The aqueous phase was extracted with eight 100 ml portions of dichloromethane, and the combined extracts were dried over sodium sulfate, filtered, and evaporated. The residue was recrystallized from toluene/hexane (1:1), whereby 6.8 g (75%) of 1-hydroxymethyl-4-chloropyrazole having a melting point of 68°–71° C. were obtained.

(b) 2.65 g of 1-hydroxymethyl-4-chloropyrazole in 20 ml of dichloromethane were added dropwise to a solution of 3 ml of thionyl chloride in 10 ml of dichloromethane at 0° C. The mixture was stirred at 0° C. for 1 hour and then left to stand at 25° C. for 2 hours. The solution was evaporated to dryness, and the residue was taken up in diethyl ether. After filtration to remove a small amount of solid, the filtrate was evaporated, whereby 2.8 g (93%) of 1-chloromethyl-4-chloropyrazole in the form of an oil were obtained.

EXAMPLE 25

Preparation of 1-[4-[2-hydroxy-3-(isopropylamino)propoxy]phenoxymethyl]-4-pyrazolecarbonitrile p-toluenesulfonate In a manner analogous to that described in Example 18, from 1.42 g of 1-chloromethyl-4-cyanopyrazole, 2.4 g (48%) of 1-[4-[2-hydroxy-3-(isopropylamino)propoxy]phenoxymethyl]-4-pyrazolecarbonitrile p-toluenesulfonate having a melting point of 97°–100° C. (from isopropanol/ethanol) were obtained.

The 1-chloromethyl-4-cyanopyrazole used as the starting material can be prepared as follows:

(a) 8.5 g of 4-cyanopyrazole and 10 ml of 40% formalin solution in 20 ml of water were left to stand at 25° C. for 2 hours. The mixture was extracted with ethyl acetate. The ethyl acetate extract was dried over sodium sulfate, filtered, and evaporated. The residue was recrystallized from ethyl acetate/hexane, whereby 10 g (89%) of 1-hydroxymethyl-4-cyanopyrazole having a melting point of 110°–114° C. were obtained.

(b) The foregoing hydroxymethyl compound was treated with thionyl chloride in a manner analogous to that described in Example 24(b), whereby 11.4 g (98%) of 1-chloromethyl-4-cyanopyrazole in the form of an oil were obtained.

EXAMPLE 26

Preparation of 1-isopropylamino-3-[4-[(2H-1,2,3-triazol-2-yl)methoxy]phenoxy]-2-propanol hydrochloride In a manner analogous to that described in the first paragraph of Example 1, from 333 mg of 4-[(2H-1,2,3-triazol-2-yl)methoxy]phenol, 350 mg (59%) of 1-isopropylamino-3-[4-[(2H-1,2,3-triazol-2-yl)methoxy]phenoxy]-2-propanol hydrochloride having a melting point of 141°–144° C. (from isopropanol) were obtained.

The starting material can be prepared as follows:

(a) 4.0 g of 1,2,3-triazole and 15 ml of 40% formalin solution were left to stand at 25° C. for 2 hours. The solution was then extracted with ten 50 ml portions of dichloromethane. The combined dichloromethane extracts were dried over sodium sulfate, filtered, and evaporated to dryness. The semi-solid residue was dissolved in the minimum amount of boiling diethyl ether and then left at 0° C. for 2 days, whereby 1.55 g (27%) of 2-hydroxymethyl-1,2,3-triazole having a melting point of 63°–67° C. were obtained.

(b) 0.99 g of 2-hydroxymethyl-1,2,3-triazole was dissolved in 5 ml of thionyl chloride. After 5 minutes, the solution was evaporated to dryness under reduced pressure and at a temperature below 25° C. The resulting crude 2-chloromethyl-1,2,3-triazole hydrochloride was dissolved in 5 ml of dimethylformamide, and the solution was added to a solution of 2.0 g of 4-benzyloxyphenol in 20 ml of dimethylformamide which had been stirred for 5 minutes with 0.96 g of a 50% sodium hydride dispersion in mineral oil. The mixture was stirred at 60° C. for 0.5 hour and then evaporated to dryness. The residue was partitioned between 2 N sodium hydroxide solution and ethyl acetate. The organic phase was separated, dried over sodium sulfate, filtered, and evaporated. The residue was dissolved in boiling petroleum ether (60°–80° C.), filtered while hot, and the filtrate was cooled to bring about crystallization. The crystals were removed by filtration, whereby 1.03 g ( 37%) of 1-benzyloxy-4-[(1H-1,2,3-triazol-1-yl)methoxy]benzene having a melting point of 69°–73° C. were obtained. After evaporation of the filtrate, 613 mg (22%) of 1-benzyloxy-4-[(2H-1,2,3-triazol-2-yl)methoxy]benzene in the form of an oil were obtained.

(c) The foregoing 1-benzyloxy-4-[(2H-1,2,3-triazol-2yl)methoxy]benzene was debenzylated by catalytic hydrogenation in a manner analogous to that described in Example 1(b), whereby 390 mg (94%) of 4-[(2H-1,2,3-triazol-2-yl)methoxy]phenol were obtained.

EXAMPLE 27

Preparation of 1-isopropylamino-3-[4-[(1H-1,2,3-triazol-1-yl)methoxy]phenoxy]-2-propanol hydrogen maleate In a manner analogous to that described in the first paragraph of Example 1, from 577 mg of 4-[(1H-1,2,3-triazol-1-yl)methoxy]phenol, 350 mg (27%) of 1-isopropylamino-3-[4-(1H-1,2,3-triazol-1yl)methoxy]phenoxy]-2-propanol hydrogen maleate having a melting point of 98°–101° C. (from isopropanol/ethanol) were obtained.

The starting material can be prepared as follows:

The 1-benzyloxy-4-[(1H-1,2,3-triazol-1-yl)methoxy]benzene, prepared as described in Example 26(b), was debenzylated by catalytic hydrogenation in a manner analogous to that described in Example 1(b), whereby 690 mg (99%) of 4-[(1H-1,2,3-triazol-1-yl)methoxy]phenol having a melting point of 157°–163° C. were obtained.

EXAMPLE 28

Preparation of 1-isopropylamino-3-[4-(1-pyrazolyl)methylthio]phenoxy]-2-propanol hydrogen maleate In a manner analogous to that described in the first paragraph of Example 1, from 4-[(1-pyrazolyl)methylthio]phenol, 1-isopropylamino-3-[4-[(1-pyrazolyl)methylthio]phenoxy]-2-propanol hydrogen maleate having a melting point of 83°–87° C. (from isopropanol) was obtained.

The 4-[(1-pyrazolyl)methylthio]phenol used as the starting material is prepared by reacting 4-mercaptophenol with 1-chloromethylpyrazole in the presence of potassium carbonate and in dimethylformamide at room temperature. The 4-[(1-pyrazolyl)methylthio]phenol melts at 119°–122° C.

The following Examples illustrate typical pharmaceutical preparations containing the substituted phenoxyaminopropanol derivatives provided by the invention:

EXAMPLE A

Tablets containing the following ingredients can be produced in a conventional manner:

| Ingredient | Per tablet |
|---|---|
| A substituted phenoxy-aminopropanol derivative of the invention | 25 mg |
| Lactose | 103 mg |
| Starch | 61 mg |
| Magnesium stearate | 11 mg |
| Total weight | 200 mg |

EXAMPLE B

A capsule formulation containing the following ingredients can be produced in a conventional manner:

| Ingredient | Per capsule |
|---|---|
| A substituted phenoxy-aminopropanol derivative of the invention | 25 mg |
| Lactose | 106 mg |
| Starch | 20 mg |
| Talc | 9 mg |
| Total weight | 160 mg |

This capsule formulation is suitably filled into No. 4 hard gelatin capsules.

I claim:

1. A compound of the formula

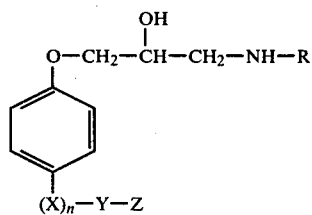

wherein R is lower alkyl, X is oxygen or sulfur, n is the integer zero or 1, Y is methylene, ethylene or propylene, or, when n is zero, Y can also be a group of the formula —CH=CH—C*H₂—  (a)

wherein the double-bond is trans and the carbon atom marked with an asterisk is linked to Z, and Z is a 5-membered aromatic heterocyclic ring selected from the group consisting of 1-imidazolyl, 1H-1,2,4-triazol-1-yl, 1H-1,3,4-triazol-1-yl, 1H-1,2,3-triazol-1-yl, 2H-1,2,3-triazol-2-yl, 1-pyrazolyl, 4-halo-1-pyrazolyl, 4-phenyl-1-pyrazolyl, 1-benzimidazolyl, 2H-benzotriazol-2-yl, 4,5,6,7-tetrahydro-2H-benzotriazol-2-yl, and 1H-indazol-1-yl, the heterocyclic ring is linked to Y via a nitrogen atom and may be substituted by halogen, lower alkyl, lower alkoxy, phenyl, cyano or carboxamido or on adjacent carbon atoms by a group of the formula

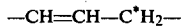

—(CH₂)₄—  or  —CH=CH—CH=CH—
  (b)              (c)

or a pharmaceutically acceptable acid addition salt thereof.

2. A compound in accordance with claim 1, wherein R is isopropyl or tert.butyl, X is oxygen, n is 1 and Y is methylene or a pharmaceutically acceptable acid addition salt thereof.

3. A compound in accordance with claim 1, wherein Z is 1-imidazolyl, 1H-1,2,4-triazol-1-yl, 2H-1,2,3-triazol-2-yl, 1-pyrazolyl or 4-halo-1-pyrazolyl, or a pharmaceutically acceptable acid addition salt thereof.

4. A compound in accordance with claim 1, wherein R is isopropyl, X is oxygen, n is 1, Y is methylene and Z is 2H-1,2,3-triazol-2-yl or 4-chloro-1-pyrazolyl, or a pharmaceutically acceptable acid addition salt thereof.

5. A compound in accordance with claim 1, 1-[4-[(4-chloro-1-pyrazolyl)methoxy]phenoxy]-3-isopropylamino-2-propanol or a pharmaceutically acceptable acid addition salt thereof.

6. A compound in accordance with claim 1, 1-isopropylamino-3-[4-[(2H-1,2,3-triazol-2-yl)methoxy]-phenoxy]-2-propanol or a pharmaceutically acceptable acid addition salt thereof.

7. A compound in accordance with claim 1 selected from the group consisting of
1-isopropylamino-3-[4-[2-(1-pyrazolyl)ethoxy]phenoxy]-2-propanol,
1-[4-[2-(1-imidazolyl)ethoxy]phenoxy]-3-isopropylamino-2-propanol,
1-[4-[2-(1-benzimidazolyl)ethoxy]phenoxy]-3-isopropylamino-2-propanol,
1-isopropylamino-3-[4-[2-(1H-1,2,4-triazol-1-yl)ethoxy]phenoxy]-2-propanol,
1-tert.butylamino-3-[4-[2-(1-pyrazolyl)ethoxy]phenoxy]-2-propanol,
1-isopropylamino-3-[4-[3-(1-pyrazolyl)propoxy]-phenoxy]-2-propanol,
1-isopropylamino-3-[4-[3-(1H-1,3,4-triazol-1-yl)propoxy]phenoxy]-2-propanol,
1-isopropylamino-3-[4-[2-(4-phenyl-1-pyrazolyl)ethoxy]phenoxy]-2-propanol,
1-isopropylamino-3-[4-[2-(4-chloro-1-pyrazolyl)ethoxy]phenoxy]-2-propanol,
1-[4-[2-(1-imidazolyl)ethyl]phenoxy]-3-isopropylamino-2-propanol,
1-isopropylamino-3-[4-[2-(1-pyrazolyl)ethyl]phenoxy]-2-propanol,
1-isopropylamino-3-[4-[2-(1H-1,2,4-triazol-1-yl)ethyl]-phenoxy]-2-propanol,
1-isopropylamino-3-[4-[2-(1-pyrazolyl)methyl]phenoxy]-2-propanol,
1-[4-[2-(1-imidazolyl)methyl]phenoxy]-3-isopropylamino-2-propanol,
1-[4-[2-(2H-benzotriazol-2-yl)ethoxy]-phenoxy]-3-isopropylamino-2-propanol,
1-[4-[2-(4,5,6,7-tetrahydro-2H-benzotriazol-2-yl)ethoxy]phenoxy]-2-propanol,
1-isopropylamino-3-[4-[3-(1-pyrazolyl)propyl]phenoxy]-2-propanol,
trans-1-isopropylamino-3-[4-[3-(1-pyrazolyl)-1-propenyl]-phenoxy]-2-propanol,
1-isopropylamino-3-[4-[2-(1-pyrazolyl)ethylthio]-phenoxy]-2-propanol, 1-[4-[2-(1H-indazol-1-yl)ethoxy]phenoxy]-3-isopropylamino-2-propanol or a pharmaceutically acceptable acid addition salt thereof.

8. A compound in accordance with claim 1 selected from the group consisting of 1-isopropylamino-3-[4-[2-(2H-1,2,3-triazol-2-yl)ethoxy]phenoxy]-2-propanol, 1-isopropylamino-3-[4-[(1-pyrazolyl)methoxy]phenoxy]-2-propanol, 1-[4-[2-hydroxy-3-(isopropylamino)propoxy]phenoxymethyl]-4-pyrazolecarbonitrile, 1-isopropylamino-3-[4-[(1H-1,2,3-triazol-1-yl)methoxy]phenoxy]-2-propanol, 1-isopropylamino-3-[4-[(1-pyrazolyl)methylthio]phenoxy]-2-propanol or a pharmaceutically acceptable acid addition salt thereof.

9. A pharmaceutical composition comprising a therapeutically effective amount of a compound of the formula

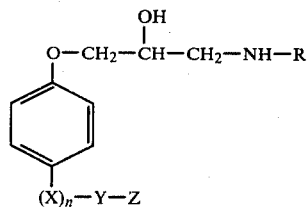

wherein R is lower alkyl, X is oxygen or sulfur, n is the integer zero or 1, Y is methylene, ethylene or propylene, or, when n is zero, Y can also be a group of the formula —CH=CH—C*H₂—  (a)

wherein the double-bond is trans and the carbon atom marked with an asterisk is linked to Z, and Z is a 5-membered aromatic heterocyclic ring selected from the group consisting of 1-imidazolyl, 1H-1,2,4-triazol-1-yl, 1H-1,2,3-triazol-1-yl, 2H-1,2,3-triazol-2-yl, 1-pyrazolyl, 4-halo-1-pyrazolyl, 4-phenyl-1-pyrazolyl, 1-benzimidazolyl, 2H-benzotriazol-2-yl, 4,5,6,7-tetrahydro-2H-benzotriazol-2-yl, and 1H-indazol-1-yl, the heterocyclic ring is linked to Y via a nitrogen atom and may be substituted by halogen, lower alkyl, lower alkoxy, phenyl, cyano or carboxamido or on adjacent carbon atoms by a group of the formula —(CH₂)₄—  or  —CH=CH—CH=CH—
(b)                      (c)

or a pharmaceutically acceptable acid addition salt thereof, together with a pharmaceutical carrier material.

10. A method for the treatment of heart diseases which comprises administration of a therapeutically effective amount of a compound of the formula

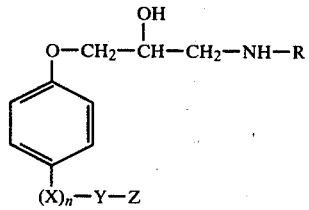

wherein R is lower alkyl, X is oxygen or sulfur, n is the integer zero or 1, Y is methylene, ethylene or propylene, or, when n is zero, Y can also be a group of the formula —CH=CH—C*H₂—  (a)

wherein the double-bond is trans and the carbon atom marked with an asterisk is linked to Z, and Z is a 5-membered aromatic heterocyclic ring selected from the group consisting of 1-imidazolyl, 1H-1,2,4-triazol-1-yl, 1H-1,2,3-triazol-1-yl, 2H-1,2,3-triazol-2-yl, 1-pyrazolyl, 4-halo-1-pyrazolyl, 4-phenyl-1-pyrazolyl, 1-benzimidazolyl, 2H-benzotriazol-2-yl, 4,5,6,7-tetrahydro-2H-benzotriazol-2-yl, and 1H-indazol-1-yl, the heterocyclic ring is linked to Y via a nitrogen atom and may be substituted by halogen, lower alkyl, lower alkoxy, phenyl, cyano or carboxamido or on adjacent carbon atoms by a group of the formula —(CH₂)₄—  or  —CH=CH—CH=CH—
(b)                      (c)

or a pharmaceutically acceptable acid addition salt thereof.

* * * * *